United States Patent [19]

Pravda

[11] Patent Number: 4,538,447
[45] Date of Patent: Sep. 3, 1985

[54] METHOD AND APPARATUS USEFUL FOR RAPIDLY DETERMINING THE MOLECULAR WEIGHT OF A FLOWING GASEOUS MATERIAL

[76] Inventor: Milton F. Pravda, 7708 Greenview Ter., Towson, Md. 21204

[21] Appl. No.: 589,009

[22] Filed: Mar. 13, 1984

[51] Int. Cl.³ ............................................. G01N 31/00
[52] U.S. Cl. ......................................................... 73/23
[58] Field of Search .......................... 73/23, 27 R, 26; 374/43, 44, 45, 54; 165/11 R, 30; 62/5

[56] References Cited

U.S. PATENT DOCUMENTS 3,165,146  1/1965  Smith et al. ........................... 73/23.1
3,173,273  3/1965  Fulton ....................................... 62/5

*Primary Examiner*—Stephen A. Kreitman

[57] ABSTRACT

The molecular weight of a pressurized flowing gas is determined by means of a vortex tube. The temperatures of the inlet gas to the tube and of its outlet hot and cold gas fractions are sensed by electromotive force-producing temperature-sensing means; the resulting e.m.f.'s are employed to ascertain differential e.m.f.'s and then to form a ratio of differential e.m.f.'s. The ratio is then converted to the molecular weight of the gas, either by means of a pre-established ratio-molecular weight relationship or converter, such as a graph of variance or a mathematical equation, or, preferably, by means of an electric circuit in which the differential e.m.f.'s, the ratio, and the molecular weight are ascertained instantaneously and the molecular weight is simply read off a meter.

10 Claims, 4 Drawing Figures

METHOD AND APPARATUS USEFUL FOR RAPIDLY DETERMINING THE MOLECULAR WEIGHT OF A FLOWING GASEOUS MATERIAL

BACKGROUND OF THE INVENTION

1. Field of the Invention

The field of the invention comprises the determination of the molecular weight of a gaseous material that is in a state of flow.

2. Description of Prior Art

Heretofore, the molecular weight of a gas, as described in chemistry text books, has been determined in slow batch-type or single test procedures, one of which comprises measuring the volume of a weighed quantity of gas at an observed temperature and pressure, and using these data in the perfect-gas equation to calculate the molecular weight. Another comprises measuring the density, pressure, and temperature and calculating the molecular weight by aid of the perfect-gas equation rearranged to show the density. Still another is the Victor Meyer air displacement. No prior art flow methods capable of measuring the molecular weight of all gases or gas mixtures are known to applicant. Regarding the use of vortex tubes, applicant is aware of U.S. Pat. No. 3,165,146 which discloses a method for regulating the temperature of an instrument housing wherein the vortex tube is disposed within the housing, and temperature-controlled air is introduced to the tube. A thermocouple inside the housing and spaced some distance from the tube is used to sense the temperature in the housing and to influence the flow of temperature-controlled air thereto. The hot gas fraction of the vortex tube is removed from the housing while the cold gas fraction is discharged therein to cool the housing interior. This method is not concerned with molecular weight determinations.

SUMMARY OF THE INVENTION

The invention is directed to the use of a conventional vortex tube for determining the molecular weight of a flowing gas. As is known, a vortex is able to separate a gas fed to it into hot and cold fractions. The invention proposes to sense the temperatures of all three gas streams; i.e., inlet gas and the two fractions, by means of sensing means, preferably electromotive force (e.m.f.)-producing sensors, then to obtain from such data differential e.m.f.'s that are proportional to the temperature differences existing between each fraction and the inlet gas, and then forming a ratio of the differentials. This ratio, it has been found, is characteristic of the molecular weight of the inlet gas, may be duplicated in repeat tests, and can be used to find the molecular weight of the inlet gas.

The invention employs a single unit to receive the data from each sensor, one at a time, and to convert the same to a temperature. The temperatures are then worked up to produce temperature differentials and the ratio, and the molecular weight is ascertained independently of the unit.

The invention provides not only an easy, simple, and convenient means of determining the molecular weight of a gas but also a rapid one, requiring only an interval of less than a minute for a reading after the apparatus has been assembled and placed in working condition. The invention is useful where the test gas flow is from a batch supply or tank, or where the flow is from a continuous source, and in the latter case there is no interruption of the flow; in either case, the determination can be made without waste or destruction of the gas. The invention is of further value to enable gas phase chemical reactions to be followed by monitoring the molecular weight of the gaseous reactant or reactant mixture; a deviation from the proper molecular weight can be ascertained quickly and corrected. In a similar way, the dangerous or excessive presence of pollutants and/or toxic gases in a given environment can be made known. Other advantages will become apparent as the description proceeds.

BRIEF DESCRIPTION OF THE DRAWINGS

The invention is illustrated in the accompanying drawings, which are diagrammatic, and in which.

DESCRIPTION OF THE SPECIFIC EMBODIMENTS

Figure 1:
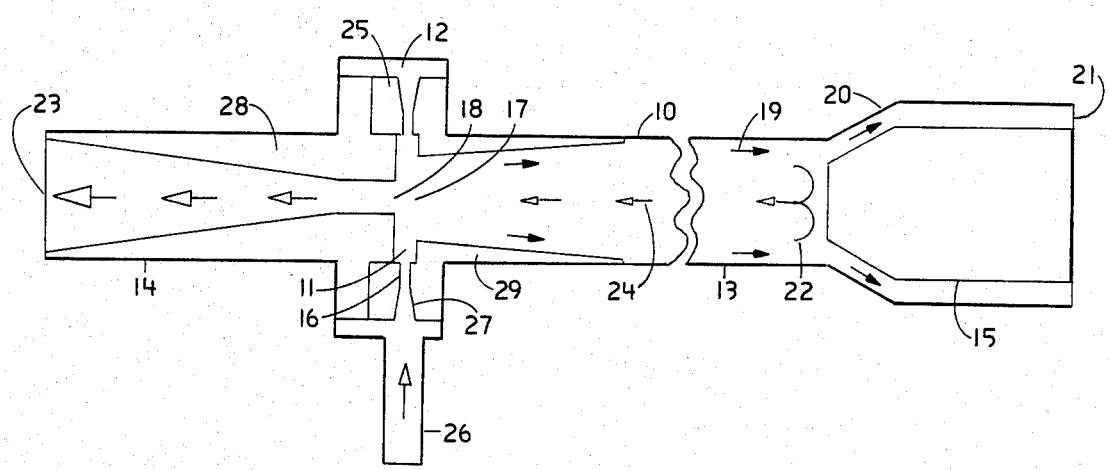
FIG. 1 is a schematic view of a conventional vortex tube showing internal arrangement.

Referring to FIG. 1, a conventional vortex tube 10 is seen as comprising a generation chamber 11, gas inlet chamber 12, a long open-ended tube 13, a short open-ended tube 14, a control valve 15, a generator 25, and a gas inlet tube 26. Nozzles 16, of which there are a plurality, introduce pressurized gas from inlet chamber 12 to chamber 11; these nozzles are to be understood as being more or less tangentially disposed relatively to chamber 11 so that they feed the gas thereto in a spinning or swirling stream or helical path; i.e., so that it has a rotational velocity. The vortex tube functions to cause the gas to flow into long tube 13, which is on one side of and in communication with chamber 11; and it will be noted that the opening 17 into such tube is larger than the opening 18 into the short tube. The spinning gas, located in a zone near the inside surface of tube 13, note 19, reaches the end 20 where it meets control valve 15 which allows part of the gas to escape; i.e., the spinning annularly located gas 19 flows out through hot end outlet 21. The remaining gas is forced to the center of tube 13 where, still spinning, it reverses, note 22, and moves back toward the short tube 14, through the latter, and is removed through cold end outlet 23. Nozzles 16 are convergent; the converging portion being formed by cone surface 27. The maximum gas velocity through nozzles 16 into chamber 11 cannot exceed sonic velocity regardless of the magnitude of the pressure in inlet chamber 12. The short open-ended tube 14 is fitted with a diffuser 28 which reduces the cold gas velocity and further reduces the cold gas temperature at outlet 23. The generator 25 has a cylindrical extension 29 which forms a transition between opening 17 and the long open-ended tube 13.

Accompanying the separation of the inlet gas into two distinct spinning streams, one inside the other and moving in opposite directions in the long tube 13, is another observed phenomenon, namely, the temperature of the outer stream is increased while that of the inner stream is decreased. The temperature changes are considerable. These phenomena are referred to as the "heat-separation" effect in U.S. Pat. Nos. 2,907,174 and 2,955,432.

In sum, and after steady state operation is attained, it may be seen that the vortex tube produces a pair of rapidly rotating, coaxially disposed fractions, comprising a warmer outer annular fraction 19 and a colder inner core fraction 24. The temperatures of these fractions may be considered with reference to the temperature of the inlet gas; thus the temperature of the hot fraction is greater than that of the inlet gas, which in turn is greater than that of the cold fraction; symbolically, $T_h > T_i > T_c$. Conveniently, the warmer fraction is simply designated as "hot", and the colder fraction as "cold".

The foregoing briefly described construction, operation, and effects of a vortex tube are disclosed in greater detail in U.S. Pat. Nos. 3,173,273 and 3,208,229, which disclosures are incorporated by reference.

Figure 2:
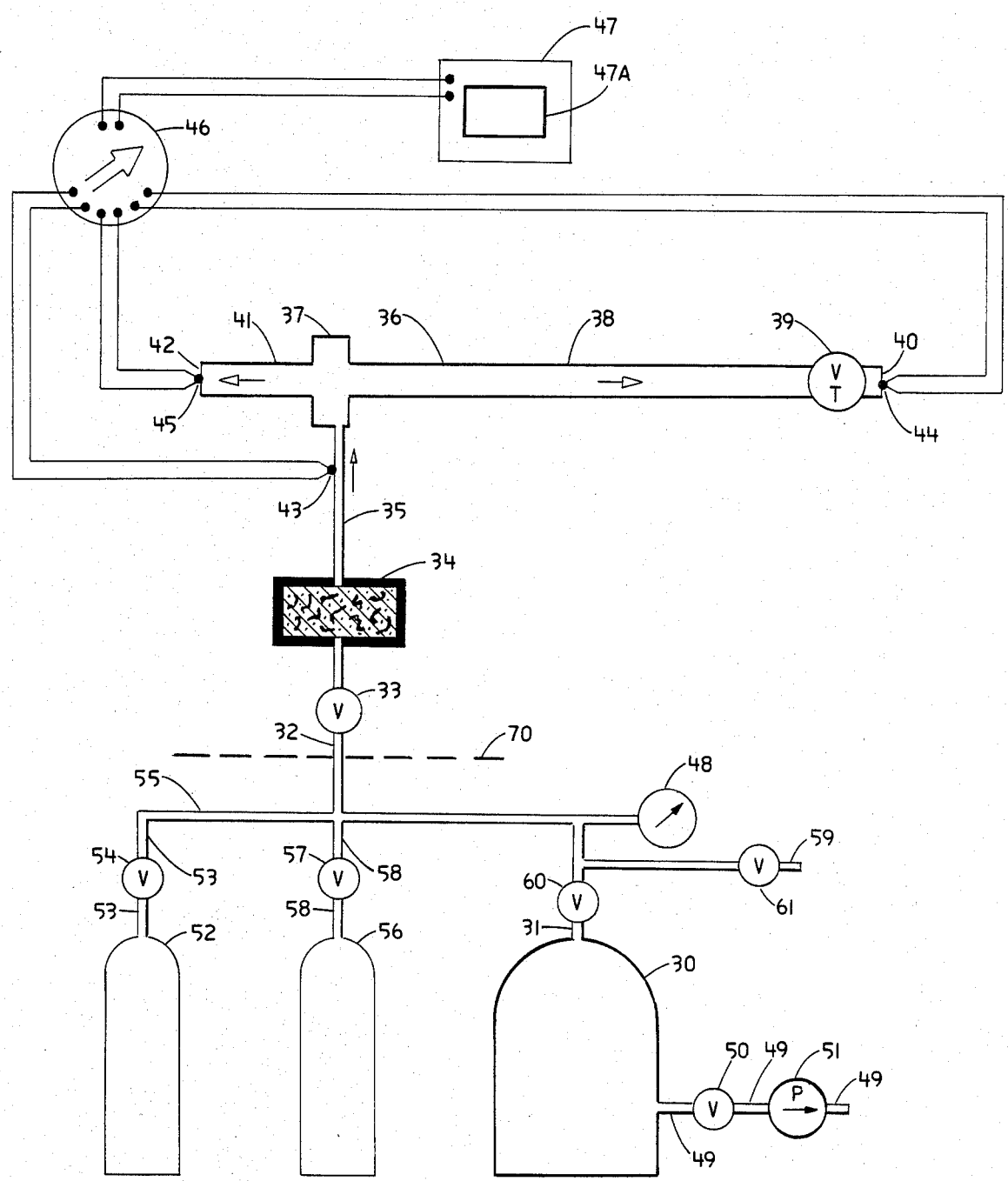
FIG. 2 is a combined gas flow and circuit diagram illustrating the passage of test gas to the vortex tube, as well as the temperature-sensing circuits associated therewith. This apparatus was used to obtain the supporting data for the molecular weight/differential temperature relationship described in Example 1.

FIG. 2 illustrates the introduction of a gas to a vortex tube and the manner in which the temperatures of the inlet and the outlet gas streams may be sensed. Briefly, pressurized test gas flows from a holding tank 30 through lines 31, 32, valve 33, and filter 34 to inlet 35 of vortex tube 36. It passes to vortex generation chamber 37 where it is expanded, given the characteristic spinning or swirling motion, and separated by means of the heat-separation effect to form the above-described hot outer and cold inner fractions. The hot fraction passes out through long tube 38, valve 39, and hot outlet 40; the cold fraction leaves through short tube 41 and cold outlet 42. Temperature-sensing means are employed to sense the temperatures of the gas streams, preferably means capable of generating an electromotive force, such as a thermocouple, which produces a small thermoelectricmotive force, on the order of millivolts, and even smaller, capable of accurate measurement. The junction of the two metals of the thermocouple is the source of the e.m.f., and the latter is proportional to the temperature sensed. In FIG. 2, thermocouples 43, 44, and 45 sense the temperatures, respectively, of the inlet gas at inlet 35, the hot gas fraction at outlet 40, and the cold gas fraction at outlet 42. Thermocouple 43 may be secured to the outer wall of inlet 35, or may extend through the wall into the gas stream; couples 44 and 45 are disposed in the gas streams. Selector switch 46 connects a given thermocouple to the unit or device at 47, comprising a Digital Trendicator, described in Example 1, having a dial 47a which gives a temperature reading for a given thermocouple millivolt value.

The pressure of the inlet gas is suitably in the range of 50 to 66 psig (3.515 to 4.640 kg/cm$^2$), and preferably 54 to 66 psig (3.796 to 4.640 kg/cm$^2$), as measured by the pressure gage 48. It will be appreciated that these pressures are below those which impart a sonic velocity to the spinning gas in the vortex tube. It has been noted that where the inlet gas is a mixture of two single gases, pressures above the described ranges tend to cause the mixture to begin to separate into its constituent gases and to cause a choking effect to occur in the converging tangential nozzles. Pressures below the described ranges tend to reduce the temperature differences and to result in inaccuracies in measurements.

Filter 34 is useful to remove any moisture not removed in the evacuation of tank 30. It may simply comprise a fine mesh screen, but may also include one or more chemical dryers. The aim is to exclude from the gas entering the vortex tube all moisture and dirt. The condition of the test gas must be taken into account to provide pretreatments that will meet this aim. Thus, some gases may require use of a coarse filter to remove larger particles of dirt, soot, rust flakes, oil, etc., that may be present; and/or means such as a valve may be present to drain water from the filter bowl where the initial gas is saturated which moisture, followed by a condenser to cool the gas and a trap to remove condensed water; and/or a further treatment may comprise passing the de-watered gas to a fine filter to remove fine particles.

The thermocouples may be chosen from those generally available, of which a number are disclosed in Handbook of Chemistry & Physics on pages E-106 to E-114 in the 56th edition or in the National Bureau of Standards, Reference Tables for Thermocouples, NBS Circular 561. Desirably, the combination of metals chosen should be one yielding the largest absolute e.m.f. for a given temperature, such as chromel-alumel, iron-constantan, copper-constantan, etc.

Throttle valve 39 of the vortex tube is set to produce a flow reversal of the inlet gas in the vortex tube. Its adjustment is described further in Example 1. Although not shown, the vortex tube is well insulated, as with fiber glass or other suitable material, to avoid heat losses. The hot and cold fractions emerging from the tube may be discarded if their amounts are small; such losses can be kept small by using a tube of small size. The fractions may be recovered and recycled to the inlet gas supply, care being taken to reintroduce them without disturbing the pressure of the gas to be tested or the exhaust pressures of the hot and cold fractions.

The test procedure comprises first evacuating holding tank 30 of any air and moisture through line 49 and valve 50 by vacuum pump 51. The test gas, as contained under pressure in a tank 52, is connected up and passed by line 53, valve 54, and line 55 to the tank 30. Enough gas is charged to tank 30 to give a reading on gage 48 somewhat more than the desired testing pressure. From tank 30 the pressurized gas is passed at ambient temperature through lines 31 and 32, valve 33, and filter 34 to the inlet 35 of the vortex tube 36.

For a given test gas, three temperature readings are measured and indicated by Trendicator 47 in response to the e.m.f.'s produced by the sensors: the inlet gas temperature $T_i$, and the hot and cold gas exit temperatures $T_h$ and $T_c$. From these there can be obtained two differential temperatures, $T_h - T_i$ and $T_i - T_c$, which for convenience are designated delta $T_h$ and delta $T_c$. Then a ratio delta $T_h$/delta $T_c$ is formed. This ratio is characteristic for the test gas, meaning that it can be obtained repeatedly for the same gas. It is then possible to obtain the molecular weight of the gas by reference to a pre-established ratio: molecular weight relationship, such as a graph of ratio versus molecular weight, or a suitable equation. A graph may be readily constructed, and suitable equations derived, as illustrated in Example 1. The ratio, delta $T_h$/delta $T_c$, can also be reversed, but for the sake of consistency it will be used as described. It can be formed from temperatures on either the Fahrenheit or centigrade scale, the former being used herein.

To run another test gas, a container for the same may be substituted for the tank 52 and the foregoing procedure repeated. The tank 56, valve 57, and line 58, which are for use in connection with Example 1, could be used for a test run, assuming of course that such tank is charged with the gas to be tested. Where the test gas is supplied from a continuous source, rather than from a batch tank, it may enter the system through line 59 and open valve 61, the valves 60, 57, and 54 being closed to avoid charging the tanks 30, 56, and 52; if desired, the latter tanks may be removed.

Any suitable gas may be tested, including the so-called inert gases of Group 0 of the Periodic Table; the normally gaseous elements of Group 7a; common gases like hydrogen, nitrogen, oxygen, and air; the various normally gaseous oxides of nitrogen and sulfur; normally gaseous hydrocarbons and chlorinated hydrocarbons; commercially important synthesized gases like ammonia and the normally gaseous "Freons" comprising fluorocarbons; also normally gaseous fluorinated and chloro-fluorinated compounds, etc. Also gases like carbon monoxide, cyanogen, hydrogen chloride, hydrogen bromide, hydrogen iodide, hydrogen sulfide, methyl amine, methyl ether, etc. Single gases or a mixture of single gases are suitable. The invention is of particular value to test a gas suspected or thought to be impure as the determined molecular weight would throw light on the question. As another example: if a piece of equipment is charged with a "Freon" type gas and records are unavailable to establish its identity, the invention can be of service by revealing its molecular weight as a step towards identifying it. In general, the gas to be tested will be known, and it may be mixed with one or more other gases. Before testing, it should of course be free of moisture and dirt. In this connection the expression "gas" or "gaseous material" is, as a matter of convenience, intended to denote a single gas, pure or impure, or a mixture of two or more single gases, or a vapor or mixture of vapors. Example 1 illustrates the utility of FIG. 2.

EXAMPLE 1

The purpose of this example was to test a number of gases of varying molecular weights in a vortex tube and to demonstrate that each produces a characteristic differential temperature ratio, delta $T_h$/delta $T_c$, and further that, as molecular weights increase, these ratios decrease. The test setup is as shown in FIG. 2, and the test procedure is as described above. Before going further, it may be well to briefly describe the various components of FIG. 2.

Vortex tube 36, comprising a brass body and stainless tubing, is a product of the Vortec Corporation, Cincinnati, Ohio, Model No. 106-2-H. It has a generation chamber diameter of 0.240 inch (0.61 cm), a cold end orifice diameter (interfacing the chamber) of 0.081 inch (0.21 cm), a hot end orifice diameter (interfacing the chamber) of 0.166 inch (0.42 cm), and an overall length of 6.5 inches (16.51 cm). The hot end orifice diameter is approximately twice the cold end orifice diameter. Four equally spaced tangential converging nozzles, each having a throat diameter of 0.019 inch (0.048 cm), extend into the generation chamber.

The Digital Trendicator, Series 410A, is a product of Doric Scientific Division of Emerson Electric Co., San Diego, Calif. As described by the manufacturer, it is a digital mullivoltmeter designed to accept a variety of inputs, including thermoelectrically-produced millivoltages, and to convert such inputs to degrees of temperature, either Fahrenheit or Centrigrade. It utilizes semiconductor technology. All digital logic, including thermocouple inputs, is contained in one of two optional ion-implanted PMOS (P-channel metal oxide semiconductor) integrated circuits. A solid-state planar LED (light-emitting diode) display is driven by on-chip decoders. Strobes provide a bright digital indication in degrees F or C on dial 47a. The device is internally compensated to correct for the slight nonlinearity of e.m.f.'s versus temperatures inherent in all thermocouples over large temperature ranges.

All thermocouples were iron-constantan. As is known, constantan is a nickel-iron alloy having a low thermal expansion. Standard tables are available for obtaining temperatures from the millivolt readings and may be found in reference works such as the Handbook of Chemistry & Physics or in NBS Circular 561. The Trendicator was calibrated to read temperatures directly from the e.m.f.'s produced by the thermocouples; the calibration work having been done by a standard calibration firm, Electronic Instrument Laboratories, Sparks, Md.

Selector switch 46 was a manually-operated device that placed one thermocouple at a time in a circuit with the Trendicator. Gas filter 34 comprised a 200-mesh screen disposed in a plastic bowl.

Several gases were tested, as listed in Table 1 below, including pure single gases, 1:1 by volume mixture of two pure single gases, air, and 1:1 by volume mixtures of air and another gas. It may be noted that tanks 52 and 56 were commercially available, thick-walled cylinders, 1 foot (30.48 cm) in diameter and 4.5 feet (137.16 cm) in height, containing gas at 3000 psig (210.9 kg/cm$^2$). In the case of a single gas as contained in tank 52, the gas was charged to tank 30, which had a volume of about 4 cubic feet (0.1132 m$^3$), until its pressure reached 70 psig (4.921 kg/cm$^2$), as recorded on pressure gage 48. From tank 30 the test gas, at ambient temperature, was passed through lines 31 and 32, valve 33, and filter 34 to the vortex tube inlet 35. All gas lines were of copper tubing. Temperature readings were recorded when pressure gage 48 read 60 psig. In the case of a mixture of single gases, such as the 1:1 mixture of nitrogen and helium, the nitrogen as contained, say, in a tank in the position of tank 52, was run into evacuated holding tank 30 to a gage pressure of 60 psig (4.218 kg/cm$^2$), and then the helium, as contained, say, in a tank in the position of tank 56, was added to tank 30 until the gage registered 120 psig (8.436 kg/cm$^2$). Tank 30 now had 1:1 or equal volumes of nitrogen and helium. During testing, however, temperature readings were recorded when pressure gage 48 read 60 psig. As will be understood, the arrangement of valves 33, 54, 57, 60, and 61 is such as will permit the described gas transfer steps to be accomplished in a safe and effective manner.

TABLE 1

| Run No. | Test Gas | M.W. from Chemical Formula | Inlet Gas Temp $T_i$ | Hot Gas Temp $T_h$ | Cold Gas Temp $T_c$ | Delta $T_h$ ($T_h - T_i$) | Delta $T_c$ ($T_i - T_c$) | Ratio: Delta $T_h$ to Delta $T_c$ |
|---|---|---|---|---|---|---|---|---|
| 1 | He | 4.0026 | 76.7 | 151.7 | 36.4 | 75.0 | 40.3 | 1.8610 |
| 2 | N$_2$:He 1:1 | 16.01 | 73.3 | 138.6 | 24.5 | 65.3 | 48.8 | 1.3381 |

TABLE 1-continued

| Run No. | Test Gas | M.W. from Chemical Formula | Inlet Gas Temp $T_i$ | Hot Gas Temp $T_h$ | Cold Gas Temp $T_c$ | Delta $T_h$ ($T_h - T_i$) | Delta $T_c$ ($T_i - T_c$) | Ratio: Delta $T_h$ to Delta $T_c$ |
|---|---|---|---|---|---|---|---|---|
| 3 | He:Air 1:1 | 16.49 | 73.8 | 134.7 | 28.1 | 60.9 | 45.7 | 1.3326 |
| 4 | Ar:He 1:1 | 21.975 | 74.5 | 143.8 | 14.9 | 69.3 | 59.6 | 1.1628 |
| 5 | Air | 28.97 | 74.0 | 121.9 | 26.1 | 47.9 | 47.9 | 1.0000 |
| 6 | Ar | 39.95 | 69.4 | 126.9 | 7.9 | 57.5 | 61.5 | 0.9350 |
| 7 | CF$_4$:Air 1:1 | 58.485 | 73.4 | 98.7 | 41.8 | 25.3 | 31.6 | 0.8006 |
| 8 | CF$_4$ | 88 | 70.8 | 87.0 | 43.2 | 16.2 | 27.6 | 0.5870 |

For each gas tested, there was measured and recorded the inlet gas temperature $T_i$, the hot gas fraction exit temperature $T_h$, and the cold gas fraction exit temperature $T_c$. About 10 seconds were required to get all readings. The table also gives the temperature differentials, $T_h - T_i$, or delta $T_h$, and $T_i - T_c$, or delta $T_c$, and the ratios, delta $T_h$/delta $T_c$. All temperatures are in °F., the 1:1 gas mixtures are on a volume basis, and M.W. stands for molecular weight. Referring to the table, the molecular weight of each gas mixture was calculated by averaging. For example, in the case of the nitrogen:-helium mixture of Run 2, the molecular weight of nitrogen is 28.0134 and helium is 4.0026, giving a total of 32.0160, but since the mixture is only half nitrogen and half helium, its molecular weight is 32.0160/2 or 16.008 or 16.01.

As can be seen, a characteristic delta $T_h$/delta $T_c$ ratio is obtained for a given gas molecular weight. Further, as the molecular weight increases, the ratio decreases. This relationship may be expressed graphically in a graph or plot of ratio versus molecular weight, as in FIG. 3, so that, for any subsequent gas tested, one can obtain its molecular weight from such graph after measuring the three temperatures noted in Table 1 and determining from them the delta $T_h$/delta $T_c$ ratio. The graph may be seen as a pre-established ratio-to-molecular weight relationship or converter useful to convert ratio to molecular weight. For practical use, the graph will be drawn on large-sized graph paper using appropriately large scales for ratio and molecular weight so that molecular weight may be read accurately to two decimal places.

Figure 3:
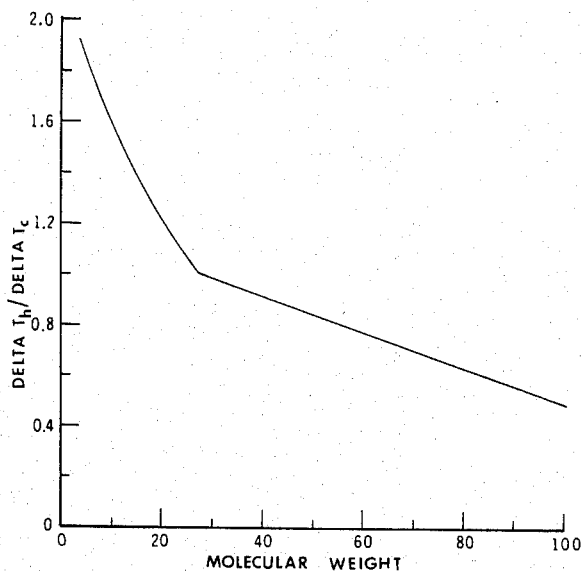
FIG. 3 is a graph of reduced size of ratio versus molecular weight.

The curve of FIG. 3 is a straight line above a molecular weight of about 30, say from 30 to about 110; and it is a curved line below about 30, say from 4 to 30. It is possible to express the relationship mathematically by deriving an equation based on the runs of Table 1 and preferably to derive two equations, one applicable to the straight line part of the curve and one to the curved part. For the straight line part, molecular weight and ratio values for two runs are taken, and the values for each run are inserted in the general equation: $y = kx + c$, where x and y are the molecular weight and ratio values, and k and c are constants. Two equations are set up and solved for k and c, leading to an equation of the form Ratio of delta $T_h$/delta $T_c = 1.2243 - 0.007242 \times$ M.W. (1)

If the value of the ratio is known, this equation can be solved for molecular weight.

For the curved part of the curve, an equation is derived in the following way: first, from the ratio and molecular weight data of Run Nos. 1–5 of Table 1, the ratio and molecular weight values for two runs are chosen. Each of these is then substituted in a general equation of the form, log $y = kx + c$, to give two equations, and these are solved for k and c. The resulting values of k and c are then substituted in the general equation, giving $$\log \frac{\text{delta } T_h}{\text{delta } T_c} = 0.3129 - 0.0108 \times \text{M.W.} \quad (2)$$

If the log of the ratio is known, the equation can be solved for M.W.

As the Trendicator 47 produces temperature readings for given inputs of e.m.f., it follows that the delta $T_h$/delta $T_c$ ratio, which is characteristic for each gas, is proportional to a characteristic ratio of delta $V_h$/delta $V_c$, where $V_h$ and $V_c$ are voltages. More particularly, for each sensed temperature $T_i$, $T_h$, and $T_c$, the Trendicator produces a corresponding compensated e.m.f. designated $V_i$, $V_h$, and $V_c$; and for the values of delta $T_h$ (or $T_h - T_i$) and delta $T_c$ (or $T_i - T_c$) there are corresponding values of delta $V_h$ (or $V_h - V_i$) and delta $V_c$ (or $V_i - V_c$). And for the delta $T_h$/delta $T_c$ ratio, a corresponding delta $V_h$/delta $V_c$ ratio may be produced. In other words, the delta $V_h$/delta $V_c$ ratio is derivable in the same way as the temperature ratio but uses e.m.f. values instead of temperatures. In this example, e.m.f. values were produced but not recorded.

In FIG. 2 the gas fractions leaving the vortex tube through outlets 40 and 42 were simply discarded as the amounts were very small. In sustained practical use of the tube, provision would be made to recycle the exiting gases, or, in the case of a toxic gas, to recapture it.

Valve 39 was partly open in order to assure a flow reversal in the vortex tube. This valve controls the amount of hot gas exiting from outlet 40, and also the amount of cold gas leaving outlet 42. The particular setting used for the valve was one that led to a delta $T_h$/delta $T_c$ ratio of 1.00 using air as the test gas, and this setting was used throughout. At a ratio of 1.00 the long tube 38 was found to be decidedly warm to the touch and the short tube 41 decidedly cool, and it was convenient to check the operation of the vortex tube by touching these outlet tubes. The setting is illustrated by Run 5 where, with air as the test gas, the hot gas temperature was 121.9° F. and the cold gas temperature was 26.1° F. At such setting it can be shown that substantially equal amounts of air exit from the hot and cold ends of the tube. For field use, air is a convenient gas to obtain the desired setting as it is available generally in compressed form. It will be understood that other settings could be employed, and test gases other than air could be employed to obtain them.

This concludes Example 1.

EXAMPLE 2

Figure 4:
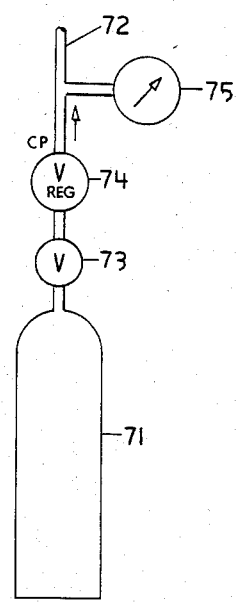
FIG. 4 is a view of part of the apparatus used in Example 2 to determine the reliability of the invention.

The purpose of this example was to demonstrate the reliability of the invention by determining the molecular weight of two gaseous materials, whose identity was unknown at the time of testing but which became known afterwards, to see if the observed molecular weights conformed to the actual or calculated values. A second party was asked to supply three tanks of pressurized gases as follows:

- a tank of pure nitrogen
- a tank, labeled No. 1, of two pure single gases mixed together in equal volumes, the identity of neither being revealed
- a tank, labeled No. 2, of a pure single gas whose identity was not revealed The test apparatus was the same as in FIG. 2 except that everything below the broken line 70 was omitted; instead, the tank 71 of FIG. 4 was substituted, with line 72 being connected to line 32 of FIG. 2. Tank 71 was a commercially available cylinder containing nitrogen under pressure and equipped with a conventional valve 73. A pressure regulator 74 was installed to regulate the pressure; and, once set, it operated at constant pressure, denoted by "CP" in FIG. 4. Pressure gage 75 was connected to line 72 as shown.

For the test, valve 73 was opened and the regulator set to give a reading of 60 psig on gage 75. Valve 39 on the hot side of the vortex tube was adjusted to give a delta $T_h$/delta $T_c$ ratio as close as possible to 1.0. The nitrogen, in this case, was merely employed to adjust valve 39. A set of temperature readings was taken and is reported in Table 2 in °F.

Then the nitrogen tank was disconnected, removed, and replaced by tank No. 1 of the same size, containing the unknown No. 1. The pressure regulator was attached, the pressure adjusted to read 60 psig on the gage, and another set of readings taken. They are recorded in Table 2.

Tank No. 1 was removed and replaced by tank No. 2 containing unknown No. 2, and another set of readings was obtained at 60 psig and recorded. Table 2 follows:

TABLE 2

| Run No. | Test Gas | Inlet Gas Temp $T_i$ | Hot Gas Temp $T_h$ | Cold Gas Temp $T_c$ | Delta $T_h$ ($T_h - T_i$) | Delta $T_c$ ($T_i - T_c$) | Ratio: Delta $T_h$ to Delta $T_c$ |
|---|---|---|---|---|---|---|---|
| 1 | Nitrogen | 71.0 | 118.7 | 23.6 | 47.7 | 47.4 | 1.0063 |
| 2 | Gas No. 1 | 73.6 | 112.9 | 26.3 | 39.3 | 47.3 | 0.8309 |
| 3 | Gas No. 2 | 72.5 | 92.3 | 30.2 | 19.8 | 42.3 | 0.4681 |

When the ratios for Gases Nos. 1 and 2 were substituted in equation (1) above, molecular weight values of 54.32 and 104.42, respectively, were obtained.

After several days, the described second party identified the unknowns as follows: No. 1 was a 1:1 mixture by volume of difluoroethane and propylene ($CH_3CHF_2$ and $CH_3CH=CH_2$), having a calculated molecular weight of $(66.06+42.09)/2$ or 54.08; and No. 2 was chlorotrifluoromethane ($CClF_3$), having a calculated molecular weight of 104.46. The determined molecular weight of No. 1 was 0.240 or 0.444% higher than the formula value, being 54.32; the determined molecular weight of No. 2 was 104.42, or 0.04 or 0.0383% lower than the calculated value. In both cases the deviation from the calculated value was less than 0.5%.

This concludes Example 2.

Of pertinent interest is the application of the invention to determine the molecular weight of a gaseous reactant mixture which is used in a gaseous phase reaction to produce one or more products and wherein the reaction is incomplete, leaving an amount of unreacted reactants which it is desired to reuse. Initially, the proper proportions of the reactant mixture are known accurately; but, after the unreacted components are recycled and mixed with fresh reactants, the resulting mixture is changed such that the reactant proportions may no longer be proper for the reaction. A rapid determination of the molecular weight of the last-named mixture by means of the invention will be of value since it will signal whether or not it is necessary to add more of one reactant or another before sending the mixture to the reactor.

One such gas phase reaction is the high temperature-high pressure synthesis of ammonia from nitrogen and hydrogen, $$N_2 + 3H_2 \rightarrow 2NH_3, \tag{3}$$

by affording an easy and convenient way to control accurately the proportions of nitrogen and hydrogen. This reaction is carried out at 400° to 600° C., a pressure of 100 to 1000 atmospheres, and in the presence of a heterogeneous catalyst like iron plus iron oxide. As the equation shows, the reactant mixture consists of 1 mol or volume of nitrogen and 3 mols or volumes of hydrogen, or 25% nitrogen and 75% hydrogen, and has a molecular weight of $(28 \times 25\%)$ plus $(2 \times 75\%)$ or 8.5 at standard conditions. If the mixture has a molecular weight above 8.5, excess nitrogen is considered to be present; while below 8.5 there is excess hydrogen. Excess reactant will not enter into the reaction; and, therefore, the energy required to bring it up to reaction temperature and pressure is wasted. The invention can be of benefit to this reaction in two ways. First, it can insure the correct proportion of nitrogen and hydrogen in the original reactant mixture, and this may be done by passing the mixture to the inlet of the vortex tube and determining the molecular weight in the manner described; if it varies from the desired value of 8.5, the mixture is passed to an adjustment zone for addition of nitrogen or hydrogen, after which it is pressurized and sent to the reactor. Of course, if no adjustment is required, it is passed unaltered through the adjustment zone, or the latter is bypassed, and it is pressurized and reacted. Such determination of the molecular weight, and the adjustment of the proportions, may be performed in a continuous manner as well as batchwise.

The second way in which the invention can benefit the reaction involves the recycling of the unreacted gases. As the conversion is usually of the order of up to 25%, substantial quantities of unreacted gases are involved and, furthermore, if the amount of recycled nitrogen or hydrogen is excessive, the proportion of that gas in the reactant mixture (original mix plus recycled material) can build up rapidly and reduce the production rate. According to the invention, it is proposed that after the reaction mixture leaves the reaction zone, and after conventional separation of the ammonia product as liquid ammonia, the unreacted gases be combined with fresh charge, the pressure adjusted, the molecular weight of the resulting mixture be determined as described above, the reactant proportions be adjusted if necessary, and the process continued in an uninterrupted way.

The preceding description of ammonia synthesis is applicable to the Linde process, which employs substantially pure hydrogen from the electrolysis of water and substantially pure nitrogen from the liquefaction of air. It is also of interest in connection with the Haber process, which employs hydrogen obtained from water gas and nitrogen from producer gas.

Another reaction in which the invention may be applied is that of the U.S. contact process for making sulfur trioxide by the oxidation of sulfur dioxide, an important step in the manufacture of sulfuric acid, $$2SO_2 + O_2 \rightarrow 2SO_3 \quad (4)$$

The reaction is carried out at a preferred temperature of 425°–450° C. and a pressure in the range of 5 to 30 atmospheres. According to this equation, the reactants comprise 2 mols or volumes of sulfur dioxide and 1 mol or volume of oxygen, or 66.6% dioxide and 33.3% oxygen; but in this process, using a catalyst like platinum on a support of vanadium pentoxide, the amount of oxygen is generally in excess, usually twice the stoichometric amount, so that the reactants comprise 2 mols of each gas, or 50% dioxide and 50% oxygen. The original reactant mixture has a molecular weight of $(64 \times 50\%)$ plus $(32 \times 50\%)$ or 48. Using the method of the invention to monitor the reactant mixture, the molecular weight to be determined by the vortex tube is to be compared with this value; and a value greater than 48 signifies excess dioxide and requires addition of oxygen to the mixture, while one less than 48 signifies excess oxygen and requires more dioxide. Following adjustment of concentrations, if necessary, the mixture is pressurized and sent to the reactor.

A further reaction for employment of the invention is the buring of hydrogen in an atmosphere of chlorine to form hydrogen chloride, $$H_2 + Cl_2 \rightarrow 2HCl, \quad (5)$$

which may be carried out in a nonexplosive way at room temperature in the absence of bright sunlight. As is apparent, the reactants consist of 1 mol or volume of hydrogen and 1 mol or volume of chlorine; the molecular weight is $(2 \times 50\%)$ plus $(70.9 \times 50\%)$ or 36.5. A reactant mixture having a greater molecular weight than 36.5 has excess chlorine and requires addition of hydrogen, while one with a lower value has excess hydrogen and requires addition of chlorine.

The presence of toxic gases in an industrial or other working atmosphere may be detected and monitored. One first obtains a molecular weight value of the gases in the atmosphere in a toxic gas-free state for use as a standard of comparison; and then the working atmosphere is monitored by the present method, either on an intermittent or continuous basis, so that a determined molecular weight value differing from the standard is sufficient to alert observers to investigate and to take suitable action. This application of the invention is of interest where the atmospheric environment in question is known to be susceptible to the leakage or presence or formation of toxic gases, especially those that are odorless, like carbon monoxide, but also including other gases, particularly in small "hard-to-notice" amounts, such as the "Freons", chlorinated hydrocarbons, ammonia, acetone vapors, sulfur dioxide, methane, other normally gaseous hydrocarbons and normally liquid hydrocarbons having an appreciable vapor pressure. It is considered that the invention will be useful to monitor such atmospheres when they contain substantial proportions of toxic or pollutant gas or gases, say at least 1%, and preferably 2% or more.

Related to the foregoing application is the use of the invention to monitor the presence of high concentrations of unburned hydrocarbons in automobile exhaust gas. The latter is rather a complex mixture comprising gases brought in with the oxidizing air (nitrogen, oxygen, carbon dioxide, argon, etc.) and gases resulting from the combustion of the hydrocarbon fuel, including unused oxygen, carbon dioxide, carbon monoxide, water vapor, oxides of nitrogen, and unburned hydrocarbons. Before the mixture can be tested, it must be freed of all moisture and all dirt, both coarse and fine. Then its molecular weight may be determined as above described. A molecular weight for use as a standard must be obtained using a moisture-free dirt-free hydrocarbon-free exhaust gas, and the two values compared. It is contemplated that the presence of higher concentrations of unburned hydrocarbons, say 5000 p.p.m. and up, may be detected. Exhaust gases resulting from other fuels and from any internal combustion engine may be so monitored.

In connection with test gases that are, or may contain, toxic materials and/or pollutants which may be corrosive to the vortex tube material, it is advisable to use a tube, or parts thereof, made of a chemically inert material, such as a plastic or ceramic. Useful plastics include Teflon, which is a fluorocarbon resin, and methyl methacrylate. Regardless of the material, the tube may have a varying capacity, ranging from less than 1 to 100 or more cubic feet per minute (0.47 to 47.19 liters/sec.).

It will be understood that the invention is capable of obvious variations without departing from its scope.

For example, the temperature sensing means may include resistance temperature detectors (RTD) with suitable circuit modifications to produce e.m.f.'s. Bead type thermistors may also be employed as the temperature sensing means. Care must be exercised to keep the temperature sensor size small in comparison to the sizes of the hot and cold fraction exists; otherwise, excessive backpressures will be experienced and the apparatus will not function as intended. This last consideration is especially important in miniaturized versions of the apparatus. The testing was conducted with the inlet gas at ambient temperature and the hot and cold fractions exiting at ambient pressure (0 psig). Inlet gas temperatures other than ambient can be used since the method only employs temperature differences between the inlet gas and the hot and cold fractions. Hot and cold fraction exit pressures other than ambient can be employed as long as the specified differential pressure between the inlet gas and hot and cold fraction exit pressures is maintained. In selecting both inlet gas operating temperature and inlet to hot/cold fraction differential pressure, choking in the tangential nozzles must be avoided and temperature sensor e.m.f.'s must produce delta V's which are sufficiently large to permit accurate measurement.

As a further example, the method described herein is shown to determine the molecular weight of a gas or gas mixture over a range of molecular weights from 4 to over 100 with one setting of the vortex tube throttle valve and for a specified inlet gas pressure. If the method is employed to measure the molecular weight over a restricted range of say from 20 to 30, it is obvious from Table 1 of example 1, that the inlet gas pressure can be reduced below the range reported herein, since the delta V's at 60 psig are a factor of 3 larger than those encountered at 60 psig at molecular weights of 88; the lower limit in the pressure range being determined by measurement inaccuracy at high molecular weights.

In the light of the foregoing description, the following is claimed:

1. In a method of operating a vortex tube by feeding a gas under pressure to an inlet of the tube and expanding the same in a vortex generation chamber to form hot and cold fractions, and wherein said fractions are separately removed from the tube, the improvement comprising determining the molecular weight of said gas by the aid of said tube and by means of the following steps:
pressurizing the inlet gas,
sensing the temperature of the gas in said inlet by means of a temperature sensor to produce an e.m.f., designated $V_i$,
sensing the temperatures of the hot and cold fractions as they emerge from the tube by means of temperature sensors to produce e.m.f.'s respectively designated $V_h$ and $V_c$,
obtaining a first differential e.m.f. $V_h - V_i$, designated delta $V_h$ that is representative of the temperature difference between the hot fraction and the inlet gas,
obtaining a second differential e.m.f. $V_i - V_c$, designated delta $V_c$, that is representative of the temperature difference between the inlet gas and the cold fraction,
forming a ratio of the delta V's,
and employing said ratio in a pre-established ratio-molecular weight converter relationship to convert the ratio to the molecular weight of the gas.

2. Method of claim 1 wherein said gaseous material is a single gas.

3. Method of claim 2 wherein the determined molecular weight of said gas deviates from the value calculated from the chemical formula thereof by a factor of less than 0.04%.

4. Method of claim 1 wherein said gaseous material is a mixture of gases.

5. Method of claim 4 wherein the determined molecular weight of said mixture deviates from the value calculated from the chemical formula thereof by a factor of less than 0.5%.

6. Method of claim 1 wherein said gaseous material is a mixture of at least two gaseous reactants which take part in a gaseous reaction, and wherein the determined molecular weight of the mixture serves as a means of controlling the proportions of reactants in said reaction.

7. Method of claim 6 wherein a reaction product is formed and some of the reactants are unreacted, and wherein prior to the determination of said molecular weight the unreacted gases are recycled to join fresh reactants.

8. Method of claim 1 wherein said gaseous material is a mixture including a toxic agent, and wherein the determined molecular weight of the mixture serves as a means of verifying the presence of said toxic agent.

9. Method of claim 1 wherein said gaseous material is a mixture obtained from the exhaust of an internal combustion engine, and wherein the determined molecular weight serves as a means of detecting the presence of excessive quantities of unburned fuel.

10. Method of claim 1 wherein said gaseous material is at a pressure of 50 to 66 psi above the hot and cold fraction exhaust pressures.

* * * * *